United States Patent [19]

Guth

[11] 4,419,577

[45] Dec. 6, 1983

[54] TEST PATTERN DEVICE FOR RADIATION DETECTOR AND METHOD OF MANUFACTURE

[75] Inventor: William R. Guth, Hoffman Estates, Ill.

[73] Assignee: Siemens Gammasonics, Inc., Des Plaines, Ill.

[21] Appl. No.: 234,656

[22] Filed: Feb. 17, 1981

[51] Int. Cl.³ .................. G01D 18/00; G02B 5/00
[52] U.S. Cl. ............................ 250/252.1; 250/505.1; 378/207
[58] Field of Search ............. 250/252.1, 363 S, 505.1, 250/515.1, 519.1; 378/207

[56] References Cited

U.S. PATENT DOCUMENTS

| 2,936,378 | 5/1960 | Jensen | 250/505.1 |
| 3,011,057 | 11/1961 | Anger . | |
| 3,745,345 | 7/1973 | Muehllenhner . | |
| 4,212,061 | 7/1980 | Knoll et al. | 250/363 S |
| 4,280,047 | 7/1981 | Enos | 250/252.1 |

OTHER PUBLICATIONS

Grossman et al., "Equally Spaced Parallel-Bar Phanton for Performance Monitoring of Scintillation Cameras", J. Nucl. Med. Tech. (Sep. 1976).
Operating Manual for Scintillation Camera Model 6480-Siemens Gammasonics, Inc. Pub. No. 710-000880/rev. C pp. 5-30 to 5-35.
Operating Manual for Scintillation Camera Model 6478-Siemens Gammasonics, Inc. Pub. No. 710-000650/rev. C pp. 5-90 to 5-98.

Primary Examiner—Janice A. Howell
Attorney, Agent, or Firm—Karl F. Milde, Jr.

[57] ABSTRACT

A test pattern device for testing scintillation cameras has a radiation transparent body member with internal mercury-filled communicating passages that define a calibrated radiation opaque test pattern. A peripheral passage serves as a mask to outline the useful field of view of the camera crystal, and expansion chambers accommodate changes in mercury volume due to temperature. The body member is made by securing a plastic cover plate to a plastic base molded with grooves to form the test pattern passages and filling ports, and then sealing the filling ports after mercury has been added to fill the passages. The invention avoids the tolerance problems associated with the manufacture of conventional lead test pattern devices.

11 Claims, 2 Drawing Figures

TEST PATTERN DEVICE FOR RADIATION DETECTOR AND METHOD OF MANUFACTURE

BACKGROUND OF THE INVENTION

1. Field of the Invention

This invention relates to a test pattern device useful in testing a radiation detector such as a scintillation camera, and a method of manufacturing the same.

2. Description of the Prior Art

Test pattern devices are used to calibrate and evaluate the performance of radiation detectors. Radiation detectors, especially nuclear radiation detectors like scintillation cameras, are widely used as medical diagnostic tools for detecting the radioactivity of an object under investigation, such as for determining the distribution of a radioactive isotope absorbed by a human body organ. Examples of scintillation camera systems to which the present invention finds application are the basic Anger-type scintillation camera (named for its inventor) described in U.S. Pat. No. 3,011,057, and improvements thereof. Radiation detectors are also used in radiation transmission applications, such as in X-ray and computed tomography diagnoses.

Test pattern devices which are known as "resolution bar patterns" serve as part of the quality control apparatus used for scintillation cameras to make quality assurance checks to monitor camera performance and detect malfunctions. These test devices comprise radiation opaque material configured in the form of a calibrated bar pattern. The test pattern device is positioned between a radiation source (such as a gamma radiation source) and the scintillation cyrstal of the camera. The test pattern device is thus exposed to radiation and the resulting scintiphotos are evaluated. Intrinsic "flood and resolution" checks (without collimator) are frequently made to verify the uniformity, linearity and intrinsic resolution of the camera. Likewise, collimated "flood and resolution" checks (with collimator) are also frequently made to uncover collimator damage (e.g. collimator septa damage) and verify collimator/camera system performance. For uncollimated checks, a mask or shield ring is used to outline the useful field of view and thereby to minimize the edge-packing artifact inherent during uncollimated operation. Such quality control checks of radiation cameras using test pattern devices are described, for example, in the operating manuals of the Siemens-Gammasonics, Inc. (2000 Nuclear Drive, Des Plaines, Ill., formerly called "Searle Radiographics, Inc.") scintillation camera models 6480 and 6478, sold under the trademarks "Pho/Gamma LEM" and "Pho/Gamma LFOV", respectively (Publication Nos. 710-000880/Rev. C and 710-000650/Rev.C).

The most frequently used material for the radiation opaque parts of prior art test pattern devices is a dense solid metal such as lead, although other materials such as tungsten powder have also been used. One prior art device is formed by machining slots to form a bar pattern in a solid lead body member. Another known device comprises lead bars arranged to form a calibrated bar pattern configuration within a closed radiation transparent body member. A typical configuration of this latter type device is the Searle Radiographics "Resolution Pattern #180-823108" which has a plurality of sets of parallel evenly-spaced bars of uniform width positioned within the plane of a plastic disc-shaped body member. The different sets of bars have different uniform spacings and widths and adjacent sets of bars are oriented perpendicularly to one another. Other configurations include patterns with continuously varying spacing, crosshatch patterns, and overlapping linear patterns which can be rotated with respect to each other to provide different Moire' effect beat frequencies.

A typical prior art test pattern device is manufactured by forming grooves in a plastic or glass radiation transparent base member, the grooves being arranged in the desired bar pattern configuration. Machined or extruded bars of lead are then fitted into the grooves. The whole is then sealed by means of a cover plate secured to the grooved base member. The sealing provides a closed structure that is convenient for consumer use and is usable in both the horizontal and vertical positions.

In order to accurately test scintillation camera performance with such a test pattern device, the lead bars must not only be precisely machined or extruded to assure their correct width, but the spacing between the bars must be accurate. Prior art methods for making test pattern devices present difficult tolerance problems. Accurate bar spacing is affected by the tolerance of the bars and the clearance required for the bar to be inserted into the slots. Such tolerance difficulties become significant when typical bar phantom spacings and widths are on the order of 2–4 millimeters.

Prior art test pattern devices also take the form of calibration masks, such as those used for developing stored data for the correction of spatial nonlinearities inherent in converting the scintillations of Anger-type cameras into position coordinate electrical signals. Example of such calibration masks are described in U.S. Pat. Nos. 3,745,345 and 4,212,061 and comprise lead radiation opaque plates having calibrated apertures or gaps. Such calibration mask test pattern devices likewise suffer from the difficulties encountered in prior art manufacturing techniques where lead is used as the radiation opaque material.

SUMMARY OF THE INVENTION

It is an object of this invention to provide an improved test pattern device for testing the performance of a radiation detector, such as a scintillation camera.

It is another object of this invention to provide a test pattern device which may have a very precise test pattern.

It is a further object of this invention to provide an improved method of manufacturing a test pattern device with eliminates the tolerance problems associated with the use of lead as the radiation opaque material in the test pattern.

In accordance with one aspect of the invention, a test pattern device is provided in which a radiation opaque material in liquid form, such as mercury, is utilized instead of a solid like lead, as a radiation opaque material. The test pattern device includes a body member having internal chambers in the form of communicating passages arranged in a desired test pattern configuration, and the liquid radiation opaque material fills the passages to define the test pattern.

In a preferred embodiment, the body member is a planar disc, and the internal chambers are configured into sets of longitudinal passages of rectangular cross-section positioned within the plane of the body member. When filled with mercury, the passages precisely define a calibrated radiation opaque bar pattern. A peripheral mercury-filled passage may advantageously serve as a mask to outline the useful field of view of the scintillation crystal, and an expansion chamber formed integrally with the peripheral passage may serve to accommodate changes in mercury volume due to temperature variations.

In another aspect of the invention, a method of making a test pattern device is provided in which a closed body member is formed (as by molding) to have internal communicating passages and a sealable filling port connecting the passages to the outside of the body member. The internal communicating passages are arranged to define the desired test pattern configuration. A sufficient quantity of radiation opaque material in liquid form, such as mercury, is then introduced into the body member through the filling port to completely fill the passages, and thereafter the filling port is sealed. The body member preferably may be formed by molding a base member with grooves for the internal communicating passages and then securing a cover plate thereto.

There has thus been outlined rather broadly the more important objects, features and advantages of the invention in order that the detailed description thereof that follows may be better understood, and in order that the present contribution to the art may be better appreciated. There are, of course, additional features of the invention that will be described more fully hereinafter. Those skilled in the art will appreciate that the conception on which this disclosure is based may readily be utilized as the basis for the designing of other arrangements for carrying out the purposes of this invention. It is important, therefore, that this disclosure be regarded as including such equivalent arrangements as do not depart from the spirit and scope of the invention.

BRIEF DESCRIPTION OF THE DRAWING

An embodiment of the invention has been chosen for purposes of illustration and description, and is shown in the accompanying drawings forming a part of the specification, wherein.

Like elements are referred to by like numerals throughout the drawings.

DESCRIPTION OF THE PREFERRED EMBODIMENT

Figure 1:
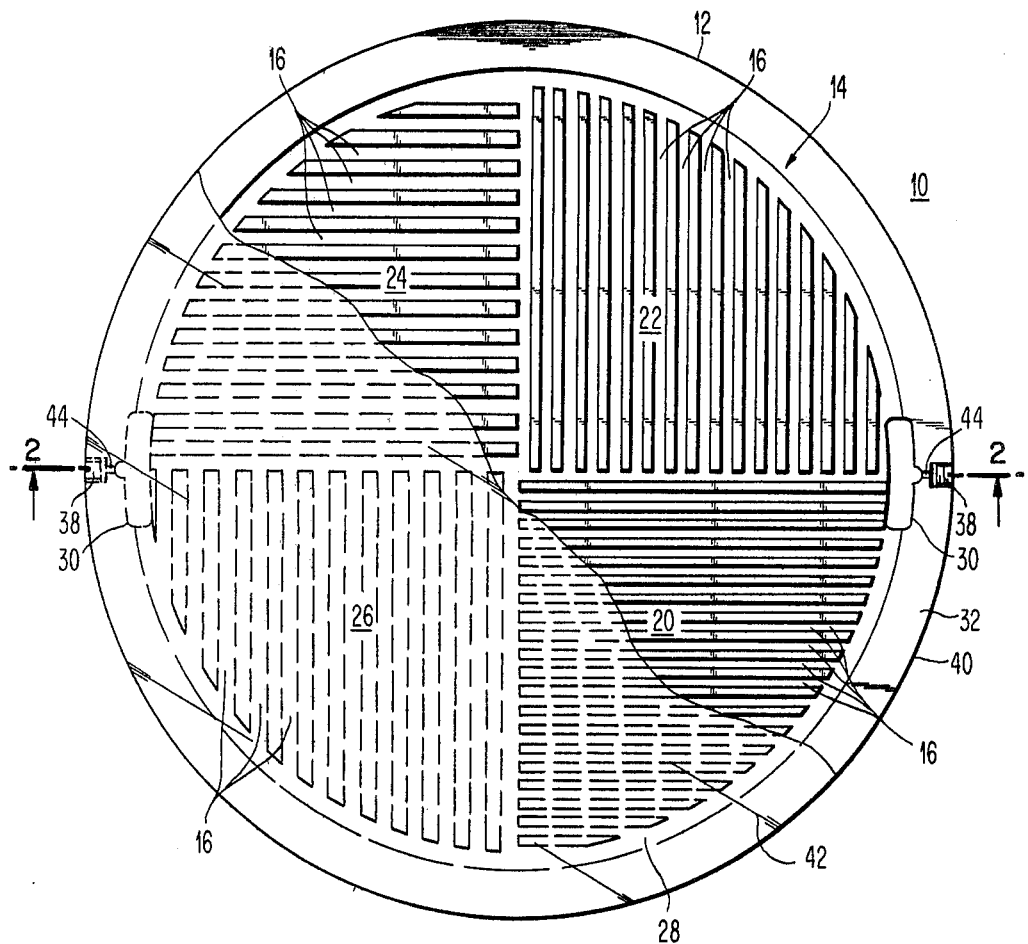
FIG. 1 is a planar view shown partially cut away, of a test pattern device formed in accordance with this invention.
Figure 2:
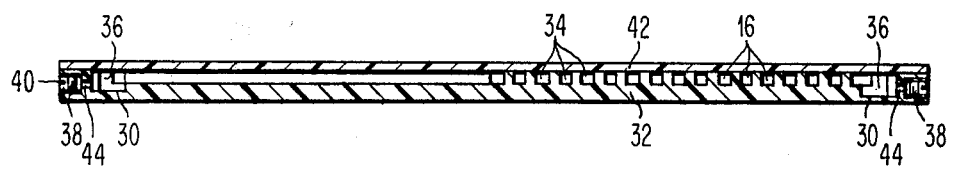
FIG. 2 is a sectional view of the device of FIG. 1 taken along the line 2—2.

FIGS. 1 and 2 show a preferred test pattern device 10 usable for making quality assurance checks for an Anger-type scintillation camera, such as for checking the camera's intrinsic resolution, collimator spatial resolution, field size and linearity.

A closed planar body member 12 made of a radiation transparent material, such as plastic, is formed in the shape of a disc with internal passages arranged in a test pattern configuration 14. The internal passages are communicating passages which are filled with a radiation opaque material in liquid form. The preferred material is mercury which is liquid at room temperature. It is possible, however, that a soluble composition such as a soluble salt of one of the heavy metals could also be used. The passages comprise longitudinal passages 16 and a circular passage 28.

The passages 16 are rectangular in cross-section and arranged in quadrant sets 20, 22, 24 and 26 within different portions of the body member 12. Each set of passages 16 comprises a plurality of parallel evenly-spaced passages of uniform width arranged within the plane of the body member. The sets of passages in the different quadrants have different spacings and widths, respectively, with dimensions selected to suit the intended use of the device. For example, in one version of the device, the passages 16 of the first quadrant set 20 have passage widths of 2 millimeters and spacings between the passages of 2 millimeters. The second quadrant set 22 has passage widths and spacings of 2.5 millimeters; the third quadrant set 24 has passage widths and spacings of 3 millimeters; and the fourth quadrant set 26 has passage widths and spacings of 3.5 millimeters. As shown in the drawings, the passages 16 of adjacent quadrant sets (for instance of the sets 20 and 22) are preferably positioned with their respective longitudinal axes oriented at right angles to each other. When filled with mercury, the passages 16 constitute the calibrated "bars" of the test pattern. The described quadrant set test pattern configuration is advantageous in that quadrant and axis resolution can be compared with a series of four scintiphotos taken with the test device rotated 90° in the same direction for each.

The body member 12 also includes a circular passage 28 extending around the periphery of the disc-shaped body member 12. The mercury-filled passage 28 serves as a mask to outline the useful field of view of the scintillation crystal, thereby aiding to minimize the previously mentioned edge-packing artifact during uncollimated testing of the camera. The peripheral passage 28 also provides a convenient communication path for mercury to flow to and from the peripheral ends of the separate passages 16. Expansion chambers 30 which are integrally positioned at diagonally opposite positions along the peripheral passage 28 act as mercury reservoirs to accommodate the changes in mercury volume due to temperature variation.

Use of a radiation opaque material in liquid form like mercury instead of a material like lead to define the test pattern 14 eliminates the problems associated with the machining or extruding of lead into bars in the prior art manufacture of test pattern devices. Mercury flows freely throughout the communicating passages formed in the body member and readily assumes the shape of the passage walls. A preferred method of manufacture for a test pattern device according to the present invention is described below.

The disc-shaped body member 12 described previously is made of a radiation transparent material, such as plastic or glass. Plastic has the advantage that it can be easily molded. In manufacture, a circular base member 32 (FIG. 2) is formed by molding plastic. The diameter of the base member is chosen based on the diameter of the scintillation crystal in the camera with which the finished test pattern device is to be used. Grooves 34 of U-shaped cross-section are formed on the upper side (as viewed in FIG. 2) of the base member 32 during the molding process to define three of the four walls of the rectangular cross-sectioned passages 16 and 28 of the test pattern described above. The grooves 34 are molded to the required precision and shape for the desired test pattern configuration. During molding, side wall tapering and internal corner radii should be minimized. Two recesses 36 are formed on the upper side of base member 32 at diagonally opposite locations along the groove that defines the peripheral passage 28 to define the wall structure for the mercury expansion chambers 30. The expansion chambers 30 are not part of the test pattern and thus can be molded with less precision. However, for accommodating thermal expansion as explained below, the recesses 30 are made deeper than the grooves 34. As shown in FIG. 1, expansion chambers 30 are molded in a bulbous shape with rounded open ends that merge into the peripheral passage 28. Filling ports 38 by which mercury can be introduced into the passages 16, 28 are molded or machined at locations on the base member 32 to connect the expansion chambers 30 and the outside edge 40 of the body member 12. A circular cover plate 42 having a diameter selected to match the diameter of the base member 32 is secured by means of an epoxy resin or the like to the grooved side of the base member 32. The cover plate 42, like the base member 32, is made of a radiation transparent material, preferably plastic. The cover plate 42 provides a fourth wall for the passages 16 and 28 and also completes the wall structure of the expansion chambers 30. The body member 12, after the cover plate 42 has been secured to the base member 32, is a closed structure having internal passages 16 and 28 and expansion chambers 30 (FIG. 1) defined by the grooves 34 and 36 (FIG. 2), respectively, and having open filling ports 38. The filling ports 38 connect the communicating passages 16 and 28 to the outside of the body member 12 for the purpose of admitting mercury into the otherwise closed structure.

A sufficient quantity of mercury to fill the communicating passages 16 and 28 is then introduced through the filling ports 38 into the interior of the body member 12. The mercury-filled passages 16 define the calibrated test pattern (the "bars") of radiation opaque material in the test pattern device. The mercury-filled peripheral passage 28 provides a mask or shield to outline the useful field of view of the scintillation crystal. When a sufficient quantity of mercury has been introduced into the interior of body member 12 to completely fill the communicating passages, the preferred two filling ports 38 are sealed with plugs 44 to prevent the escape of mercury from the body member. It may be desirable for each plug 44 to be a removable plug 44, such as a slug of plastic held in place by a threaded plastic or metal screw that mates with corresponding internal threads formed on each filling port 38 (FIGS. 1 and 2). This construction will permit the mercury to be conveniently removed from the device at a later time. Each plug 44 can also take a permanent form, however, such as a plastic globule melted or glued into the opening of each port 38. The optimum way to fill the passages with mercury may vary depending on the test pattern configuration. The number and positions of the filling ports can be varied to suit the intended filling procedure. As mentioned above, the two expansion chambers 30 provide room for variations in the volume of mercury due to increases in temperature after assembly. The device will be used in the horizontal position with the cover plate 36 facing down (opposite to that shown in FIG. 2).

The mercury is advantageously introduced into the device 10 at an elevated temperature selected to be above the highest normal operating temperature. With a sealed tube or vacuum pump attached at one filling port 38, mercury can be run into the other port 38 until the passages 28 and chambers 30 are filled. After the ports 38 are sealed, the mercury cools and contracts. The size and depth of the chambers 30 are selected such that the level of the mercury in the chambers 30 (with the device 10 in the horizontal position with the cover plate down) is above the level of mercury in the filled passages 28. This ensures that the passages 28 remain completely filled during normal operational use and that there is sufficient expansion room in chambers 30 to prevent breakage due to mercury expansion.

A test pattern device as described above that uses a radiation opaque material in liquid form to define the test pattern avoids the tolerance difficulties inherent in the manufacture of prior art lead test pattern devices. Since a radiation opaque material in liquid form like mercury readily assumes the shape of the communicating passages into which it is introduced, manufacture of a test pattern device as described above eliminates the need for individual machining or extruding lead bars in a bar pattern device and provides greater versatility in test pattern configuration.

Having thus described the invention with particular reference to the preferred form of test pattern device and method of manufacture, it will be obvious to those skilled in the art to which the invention pertains, after understanding the invention, that various changes and modifications may be made therein without departing from the spirit and scope of the invention as defined by the claims appended hereto. It will also be appreciated that the invention applies to other radiation detectors and imaging devices, such as film and other position sensitive devices.

What is claimed is:

1. A test pattern device for a radiation detector of a type having a closed body member formed with internal chambers arranged in a test pattern configuration and a radiation opaque material located within the chambers, characterized in that the internal chambers are communicating passages and the radiation opaque material is in liquid form.

2. The test pattern device as claimed in claim 1, wherein the radiation opaque material is mercury.

3. A test pattern device for a radiation detector comprising a closed body member formed with internal communicating passages arranged in a test pattern configuration, in which internal communication passages a radiation opaque material in liquid form is located, and formed with a filling port connecting the passages to the outside of the body member for introducing said radiation opaque material in liquid form into the communicating passages, which filling port is sealed with a plug to prevent the escape of said radiation opaque material in liquid form from the communication passages.

4. The test pattern device as claimed in claim 1 or 3, wherein the body member is planar and wherein the communicating passages comprise a first set of parallel longitudinal passages arranged within the body member plane.

5. The test pattern device as claimed in claim 4, wherein the communicating passages further comprise a second set of parallel longitudinal passages arranged within the body member plane with their longitudinal axes oriented transverse to the longitudinal axes of the first set of passages.

6. The test pattern device as claimed in claim 5, wherein the passages of each set of passages are evenly-spaced passages of uniform width and wherein the respective spacings and widths of the first set of passages is different from the respective spacings and widths of the second set of passages.

7. The test pattern device as claimed in claims 1 or 3, wherein the body member is planar and wherein the communicating passages further comprise four sets of longitudinal passages, the passages of each set being parallel evenly-spaced passages of uniform width arranged within the body member plane and the sets of longitudinal passages being located in different portions of the body member plane and having different respective spacings and widths.

8. The test pattern device as claimed in claim 7, wherein the different sets of passages are located in different quadrants of the body member plane and wherein the longitudinal axes of the passages of each set are oriented at right angles with respect to the longitudinal axes of the passages of the sets in adjacent quadrants.

9. The test pattern device as claimed in claim 7, wherein the body member is disc-shaped, the communicating passages include a circular passage extending around the periphery of the body member, and the device further comprises an expansion chamber formed integrally with the circular passage to accommodate changes in the volume of the radiation opaque material due to variations in temperature.

10. The test pattern device as claimed in claims 1, 2 or 3, wherein the body member is planar and wherein the communicating passages include a passage extending around the periphery of the body member plane.

11. The test pattern device as claimed in claims 1, 2 or 3, further comprising an expansion chamber to accommodate changes in volume of the radiation opaque material due to variations in temperature.

* * * * *